United States Patent [19]
Pohl

[11] Patent Number: 5,054,324
[45] Date of Patent: Oct. 8, 1991

[54] APPARATUS FOR CLAMPING A TEST SAMPLE WITHOUT ANY BENDING MOMENT

[75] Inventor: Andreas Pohl, Gross Umstadt, Fed. Rep. of Germany

[73] Assignee: Carl Schenck AG, Darmstadt, Fed. Rep. of Germany

[21] Appl. No.: 551,421

[22] Filed: Jul. 10, 1990

[30] Foreign Application Priority Data

Aug. 9, 1989 [DE] Fed. Rep. of Germany ....... 3926308

[51] Int. Cl.$^5$ .............................................. G01N 3/04
[52] U.S. Cl. ..................................................... 73/859
[58] Field of Search ................. 73/859, 860, 831, 828, 73/830

[56] References Cited

U.S. PATENT DOCUMENTS

| | | |
|---|---|---|
| 1,341,431 | 5/1920 | Morrow . |
| 2,350,577 | 6/1944 | Vordahl ............................ 73/859 X |
| 2,896,448 | 7/1959 | Haines . |
| 3,224,259 | 12/1965 | DeNicola .......................... 73/860 X |

FOREIGN PATENT DOCUMENTS

| | | |
|---|---|---|
| 671954 | 4/1939 | Fed. Rep. of Germany . |
| 2028030 | 12/1971 | Fed. Rep. of Germany . |
| 2306393 | 8/1974 | Fed. Rep. of Germany . |
| 3316218 | 11/1984 | Fed. Rep. of Germany . |
| 71217 | 11/1970 | German Democratic Rep. . |
| 250376 | 10/1987 | German Democratic Rep. . |

*Primary Examiner*—Jerry W. Myracle
*Attorney, Agent, or Firm*—W. G. Fasse

[57] ABSTRACT

Test samples, especially samples made of ceramic materials, are tested under tension and/or compression loads while simultaneously avoiding the application of a bending moment to the test sample. For this purpose, each end of the test sample is held by a holding element having spherical outer surfaces received in spherical segment recesses of clamping jaws. Each test sample end is held by its holding element in a form-locking force-transmitting manner without a direct contact between the clamping jaws and the test sample. The application of bending moments to the test sample is avoided because the cooperating spherical surfaces permit an adjustment of the testing sample into a vertical position without any canting of the test sample.

15 Claims, 4 Drawing Sheets

APPARATUS FOR CLAMPING A TEST SAMPLE WITHOUT ANY BENDING MOMENT

FIELD OF THE INVENTION

The invention relates to an apparatus for clamping a test sample without applying a bending moment to the test sample while permitting the application of a tensile and/or compression testing load to the sample.

BACKGROUND INFORMATION

Clamping devices of the above type are well known in the art. Such devices have sample holding elements with spherical outer surfaces which are received in spherical segment recesses of various types of clamping devices. Reference is made in this connection, for example, to German Patent Publication (DE-AS) 2,028,030, published on Nov. 30, 1972, and disclosing a clamping mechanism in which clamping jaws (2) are supported between sickle-shaped wedges (3) which in turn are slideable and adjustable between two clamping pressure applying elements (10) which are mounted on a base plate (9). The clamping elements (10) apply a sufficient pressure to hold the respective end of the test samples in such a way that the testing force or load can be applied to the test sample through a friction contact between the end of the test sample and the clamping jaws. Such a structure is relatively complicated and leaves room for improvement, especially with regard to avoiding the application of bending moments to the test sample.

In connection with testing samples for tensile and/or compresssion strength, it is necessary that exactly defined loads can be applied to the sample being tested. It is especially important that the test sample is not exposed to bending loads which can occur unintentionally, for example, if the test sample is canting, or when the cooperating surfaces of the clamping mechanism are mismatched, for example, due to imprecisions in the manufacturing process, especially at the points where the sample contacts the clamping jaws. Avoiding the application of bending moments to the test sample is especially important in connection with ceramic test samples which are particularly sensitive to bending loads, since ceramics are brittle.

In addition to the above mentioned German Patent Publication (DE-AS) 2,028,030, reference is made to German Patent (DE-PS) 671,954, and German Publication (DE-AS) 2,306,393. These publications illustrate efforts to avoid the application of bending moments to a test sample in a clamping mechanism of a testing machine. Both known clamping mechanisms employ cooperating spherical surfaces. However, it has been found that the known clamping mechanisms are not suitable for testing sensitive components, for example, of ceramic materials which are be tested by tensile forces and/or compression forces exclusively. The known devices either permit only the application of tensile forces as is the case with the just mentioned two publications or a complicated structure is required as is the case in the first mentioned publication (DE-AS) 2,028,030.

U.S. Pat. No. 1,341,431 (Morrow) discloses a grip for testing samples in which conical or spherical surface areas cooperate with each other. Morrow also wants to avoid the application of "lateral stress" to the test sample. Compression forces cannot be applied in the Morrow apparatus. The same considerations apply to the gripping device of U.S. Pat. No. 2,896,448 (Haines) in which, for example, sheet metal to be tested is wound partially around a split pin which in turn is held in a cylindrical hole. Haines wants to distribute the applied testing stress evenly over the entire cross-section of the specimen. However, it is not certain that bending stress can be avoided because the clamping mechanism directly contacts the sides of the specimen.

German Patent Publication (DE-OS) 3,316,218 discloses a mechanism for applying compressive loads to a test sample in a material testing apparatus whereby the cooperating surfaces are also spherical to assure a central introduction of the compressive testing force into the test sample.

East German Patent Publication 71,217, published on Nov. 5, 1970 discloses a self-centering clamping mechanism for test samples in which a conical surface of the clamp body cooperates with a movable spherical surface. A ring contact is established in this manner to assure the self centering.

East German Patent Publication 250,376, published on Oct. 8, 1987 discloses a clamping mechanism, especially suitable for testing sectional steel members, specifically the strength of welding seams between such sectional steel members. Suggestions toward the present combination are not found in the above discussed references.

OBJECTS OF THE INVENTION

In view of the foregoing, it is the aim of the invention to achieve the following objects singly or in combination:

to provide a simple clamping mechanism which is easily operable and which will avoid the application of bending moments to a test sample;

to provide a clamping mechanism capable of applying either a tension load or a compression load to a test sample while avoiding the application of bending loads in both instances;

to provide a clamping mechanism which is particularly suitable for sensitive test samples such as ceramic test samples; and to avoid a direct contact between the test sample and the clamping jaws of the clamping mechanism.

SUMMARY OF THE INVENTION

The clamping apparatus according to the invention is characterized in that sample holding elements have spherical surfaces on the outside for cooperation with corresponding surfaces on the inside of clamping jaws and further surfaces for tightly holding an end of a test sample. The rigid connection between the holding element and an end of a test sample may be accomplished, for example, in that the holding element has a surface that fits into a hole of the test sample end. Similarly, the holding element may have a hole through which the end of the test sample passes. Both instances include a form-locking connection.

The just described features of the invention using holding elements with spherical surfaces and attaching the sample end in a form-locking manner to these holding elements, assure a simple clamping structure that is easily manufactured and conveniently operable, especially for very brittle test samples. The cooperation of spherical surfaces on the clamping jaws and on the holding elements prevents the formation of bending moments, especially if the test sample is kept out of contact with the clamping jaws. The formation of bending moments is avoided during the clamping itself and also during the subsequent loading of the test sample because the ends of a test sample can assume a position which is free of any forces other than the testing force. The holding elements including their spherical surfaces, may be made of steel, ceramics, hard metals, or even of fiber composite materials, even conventional bearing balls are suitable for the present purposes.

A practical embodiment of the invention employs balls or spheres for the holding elements and these spheres are received in segment spherical recesses or ball shells in the clamping jaws, which in turn are clamped together by a holding ring or the like which presses the clamping jaws against the balls. Preferably, the clamping jaws have an outer conical or wedge-shaped surface, while the clamping or holding ring has a correspondingly shaped conical or wedging counter-surface forming an inner surface of the clamping ring for cooperating with the outer respective surface of the clamping jaws. Further, it is practical that the clamping jaws are received in or connected to force transmitting elements, such as a mounting fork secured to other components of the testing machine. The mounting fork holds the clamping jaws by a journal mounting, for example.

The mutual adjustment of the sample ends relative to each other especially under testing load applying conditions, is improved if the holding elements, specifically the spherical surfaces of the holding elements or balls and/or the spherical surfaces of the segmented recesses in the clamping jaws, are coated with a material providing a low friction coefficient. Instead, or in addition to such a coating, a lubricant may be introduced between the just mentioned surfaces.

The holding of round test samples is accomplished in a very practical manner by providing the holding elements or balls with a central through-going bore in which an end of the respective test sample is received and rigidly secured, for example, by welding or soldering or brazing, or by an adhesive bond, whereby a connection free of play is achieved between the holding element and the test sample.

For securing flat test samples to the balls it is practical to provide the holding element with a ground, ring-shaped surface and to provide a respective bore in each end of the test samples. Each bore is a through-hole, so that the holding element passes through the hole, whereby the spherical surfaces of the respective holding element project on both sides of the test sample and the ground or even polished ring shaped surface of the holding element comes to rest against a respective surface of the through-hole in the test sample. The just mentioned ring surfaces may be cylindrical or conical to form a frustum portion between spherical end portions of each holding element.

It is advantageous to select a slanting angle of the just mentioned ground ring surface and of the hole through the test sample in such a manner that these angles are small enough to provide a self-locking feature between the test sample and the holding element with regard to relative movements in a direction perpendicularly to the load application direction. Preferably, the surfaces cooperating in a self-locking manner slant in opposite directions. In other words, the self-locking surfaces at one end of the sample slant in one direction while the self-locking surfaces at the other end of the sample slant in the opposite direction. The self-locking feature makes sure that play between the holding elements and the test sample is avoided and that either tensile or compression forces can be applied to the test sample.

BRIEF DESCRIPTION OF THE DRAWINGS

In order that the invention may be clearly understood, it will now be described, by way of example, with reference to the accompanying drawings, wherein.

DETAILED DESCRIPTION OF PREFERRED EXAMPLE EMBODIMENTS AND OF THE BEST MODE OF THE INVENTION

Figure 1:
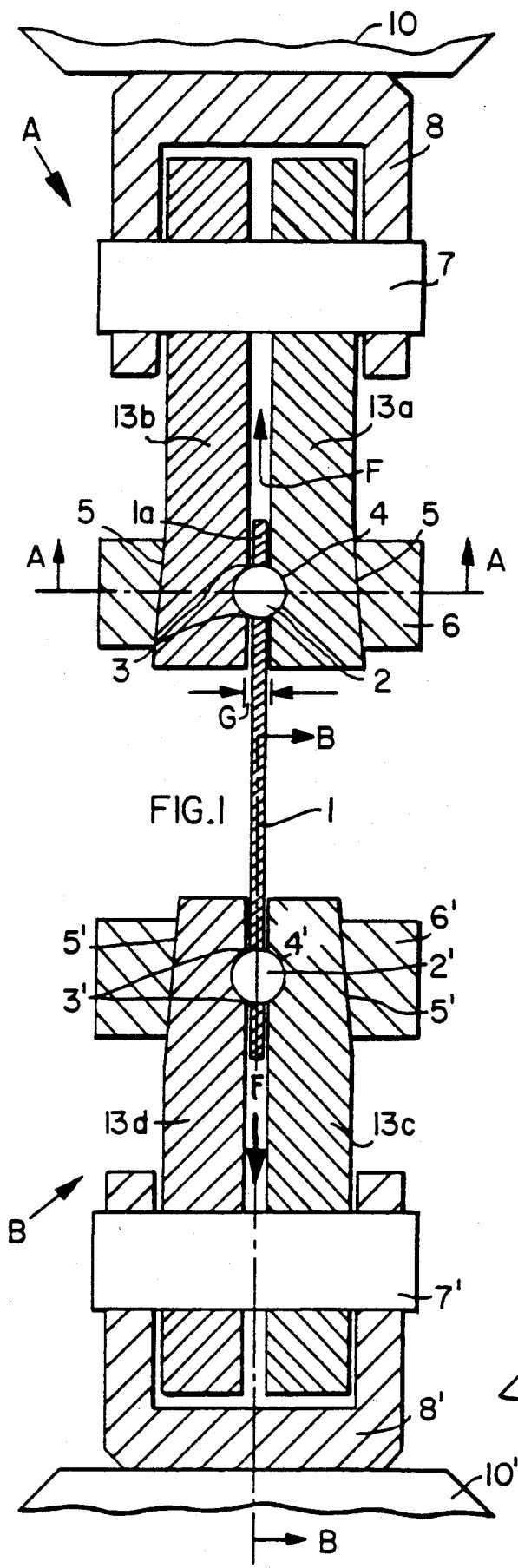
FIG. 1 is a sectional view through a clamping mechanism according to the invention for applying a tensile load to a flat test sample having a hole in each end through which a ball-type holding element passes.
Figure 1A:
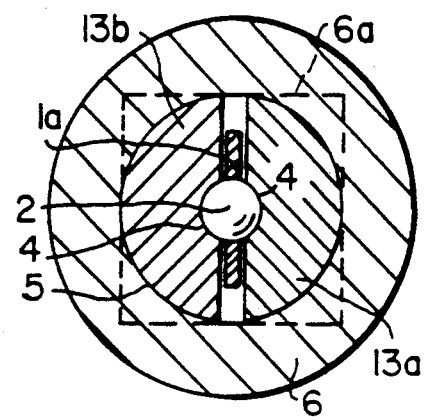
FIG. 1A is a sectional view along section line A—A in FIG. 1.
Figure 1B:
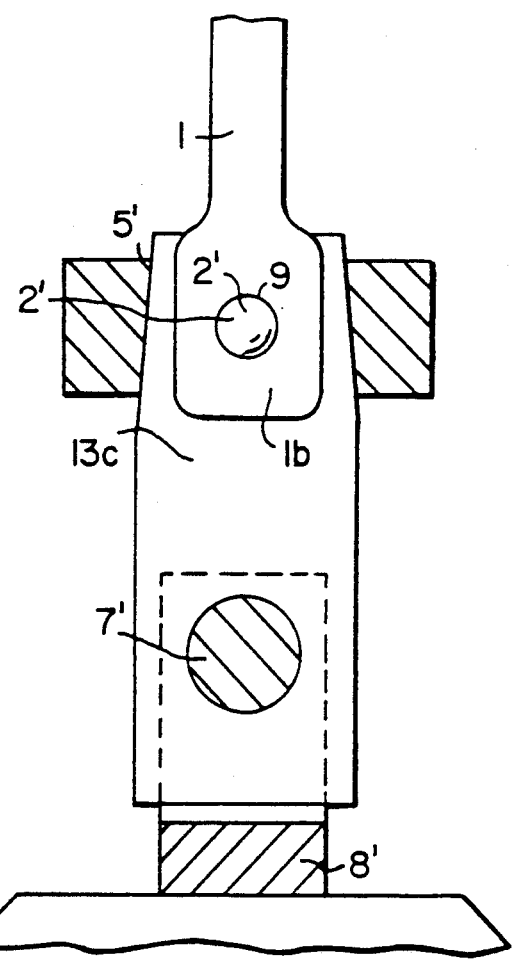
FIG. 1B is a sectional view along section line B—B in FIG. 1.

Referring to FIGS. 1, 1A, and 1B, a flat test sample 1 has an upper end 1a held in place by an upper clamping mechanism A, and a lower end 1b held in place by a lower clamping mechanism B. The upper clamping mechanism A and the lower clamping mechanism B are of similar construction, except for the wedging configuration of cooperating slanting surfaces as will be described in more detail below.

Each end 1a, 1b of the test sample 1 has a through-bore or hole 9 for indirectly securing the test sample end to the respective clamping mechanism by means of a holding element such as shown at 2, 2' in FIG. 1. In the embodiment of FIG. 1, each holding element 2, 2' has a cylindrical ring surface 3, 3' formed in its periphery or equator between two spherical segments having spherical surfaces forming a complete sphere. The spherical surfaces form clamping surfaces while the cylindrical peripheral surface forms a holding surface for the test sample. For this purpose, the cylindrical surface 3, 3' fits into the respective hole 9 in the corresponding end 1a, 1b of the test sample 1 with a form-locking fit relative to forces F effective in the longitudinal axial direction of the test sample 1. The diameter of the holes 9 and the outer diameter of the the ring surfaces 3, 3' is selected to be as small as possible for the intended purpose and will depend on the size of the particular test sample 1. The holding elements 2, 2' may be made, for example, of steel, ceramic materials, hard metals, or fiber composite materials. Even conventional spheres used in ball bearings are suitable for the present purpose. By making the through-holes 9 and the surfaces 3, 3' cylindrical, a desired distribution of the bearing pressure is achieved. However, it is quite possible to also have a line contact between the holding elements 2, 2' and the cylindrical through-hole 9. For this purpose, the holding elements 2, 2' are entirely spherical without the above mentioned cylindrical surfaces 3, 3'. Where such surfaces 3, 3' are provided, they are smoothly ground for a form-locking fit with the respective smoothly ground inner surface of the through-holes 9.

The upper clamping mechanism A comprises two clamping jaws 13a and 13b mounted in a fork 8 by a mounting pin 7. The fork 8 in turn is conventionally secured to the frame 10 of a conventional testing machine not shown in further detail. Similarly, the lower clamping mechanism B comprises two clamping jaws 13c and 13d mounted in a further mounting fork 8' by a mounting pin 7'. The lower mounting fork 8' is secured to a lower frame portion 10' of the testing machine. Each clamping jaw has a spherical segment recess 4. These recesses are arranged in each pair of clamping jaws so that the recesses face each other in a pair. The recesses 4 are deep enough to receive the corresponding holding element 2,2' in such a way that a gap G is formed between the two clamping jaws of a pair. The width of the gap G is larger than the thickness of the test sample 1 so that the latter will not directly contact the clamping jaws.

Each clamping jaw of the upper pair 13a, 13b has an outwardly flaring lower end portion to form outer wedging surfaces 5 which slant upwardly and inwardly relative to the longitudinal central vertical axis of symmetry of the apparatus. A clamping ring 6 similarly has upwardly and inwardly slanting surfaces for cooperation with the surfaces 5 to wedge the two clamping jaws of a pair to each other, thereby firmly holding without play the respective holding element 2. Similarly, each of the lower clamping jaws 13c and 13d has an upwardly tapering upper end with wedging surfaces 5', which also cooperate with a respective clamping ring 6'. In both instances the slant of the surfaces 5, 5' is such, that the respective rings 6, 6' tend to increase the clamping force in response to gravity. In any event, the clamping pressure exerted by the rings 6, 6' is sufficient to hold the holding elements 2, 2' in place without play by firmly squeezing the spherical segment recesses 4, 4' against the spherical surface of the respective holding element 2, 2'. If necessary, mechanical means may be employed to force the rings 6, 6' downwardly for a tight clamping without play For example, the rings could engage the respective surface of the clamping jaws with a threading to increase the clamping force by rotating the respective clamping ring.

In FIG. 1A the dashed line 6a shows a square cross-section which illustrates a modification of the clamping jaws. The clamping jaws 13a and 13b have circular outer surfaces. However, it is quite possible to make these clamping jaws so that they have substantially a rectangular cross-section if viewed together as indicated by the dashed line 6a. In the embodiment having clamping jaws with a rectangular cross-section, the hole in the clamping ring will also be rectangular.

In any event, the arrangement will be such that both the upper clamping ring 6 and the lower clamping ring 6' will tend to assume a lowermost clamping position under the influence of gravity. However, the invention is not limited to this arrangement. For example, it is possible that the upper slanting or conical surface 5 tapers downwardly and inwardly so that the upper ring 6 must be forced into a clamping position in an upward direction, for example, by the above-mentioned threading or by spring elements, pins, or the like. Even the two possible cross-sections shown in FIG. 1A are not critical. Other suitable configurations may be employed and the clamping jaws may even have the shape of clamping bails or the like.

The spherical surfaces of the holding elements 2, 2' and/or the spherical surfaces of the segment recesses 4, 4' can be provided with a coating to reduce friction. For this purpose the coating will have a low friction coefficient. Synthetic materials, metal carbides, nitrides, or the like are suitable for this coating purpose. In addition, or instead, a lubricant may be provided between the just mentioned spherical surfaces. In this manner it is assured that the holding elements remain movable relative to the clamping jaws in a rotational manner to thereby permit the adjustment of the vertical position of the test sample 1 and to eliminate the application of any bending moments to the test sample 1. The movability of the holding elements relative to the clamping jaws in a rotatable manner, must be assured even when the testing loads are applied to the testing sample.

Incidentally, the above mentioned frame members 10, 10' of the testing apparatus may be movable to apply the testing force, for example, as a tensile force F. The connection of the pairs of clamping jaws 13a, 13b and 13c, 13d to the force applying components of the testing machine may be varied for particular purposes. The embodiment shown in FIGS. 1, 1A, and 1B is suitable for testing the sample 1 by tensile forces F.

Figure 2:
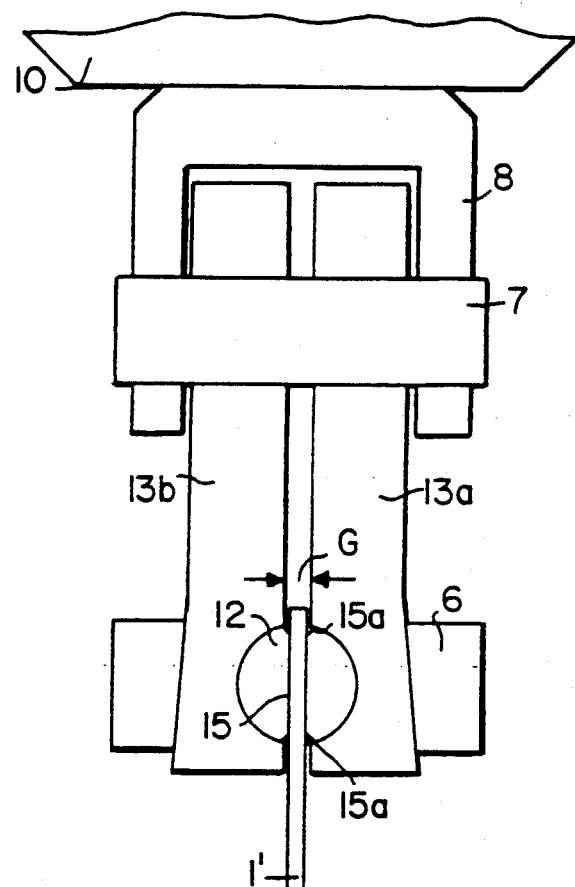
FIG. 2 is a side view similar to the sectional view of FIG. 1, showing a second embodiment according to the invention for applying tensile loads to round test samples, whereby each end passes through a through-hole in the spherical or ball-shaped holding element.
Figure 2:
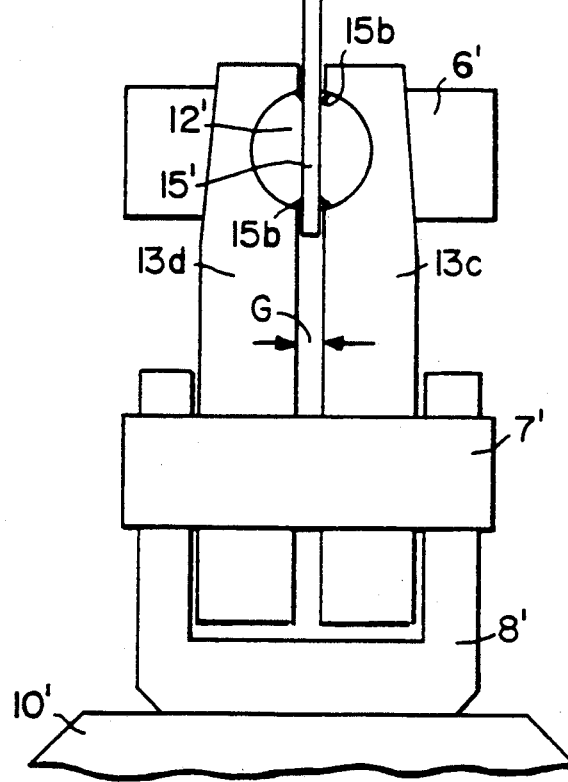

In FIG. 2 the elements which are identical to those in FIG. 1 are provided with the same reference numbers. However, in FIG. 2 the holding elements 12, 12' are spheres specifically constructed for holding a test sample 1' having a round cross-section at least at the clamping ends. The arrangement is constructed for applying tensile loads to the test sample 1'. The holding elements 12, 12' are spheres having through-bores 15, 15' respectively. The ends of the test sample 1' are rigidly secured in the through-bores 15,15' of the respective spherical holding element, for example, by heat shrinking, welding, brazing, soldering, or by an adhesive bond as shown at 15a, 15b. The heat shrink fit may be used to secure the ends of the test sample in the respective bore of the holding elements. The just described connection between the holding elements and the ends of the test sample 1' may again be released by the application of heat, for example. The spherical segment recesses in the clamping jaws and the diameters of the holding spheres are again so dimensioned that a gap G is formed between the clamping jaws to avoid contacting the test sample 1' with the clamping jaws.

Figure 3:
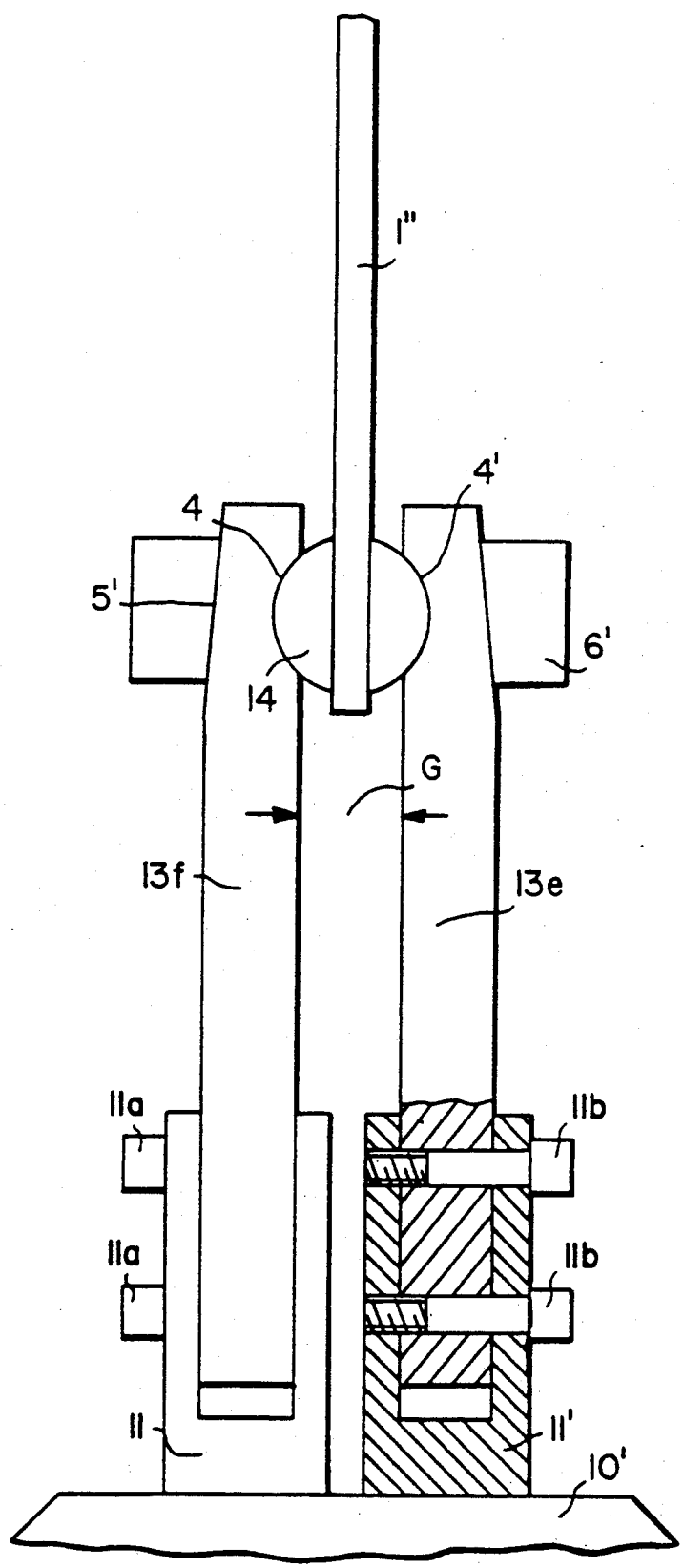
FIG. 3 illustrates a side view similar to that of FIG. 2, but showing a modification for applying tensile and/or compression testing loads to a round test sample, whereby only the lower portion of the clamping mechanism is shown and the connection between the holding elements and the end of the test sample is as in FIG. 2.

FIG. 3 illustrates an embodiment in which the mounting of the clamping jaws 13e and 13f to a machine frame member 10' is accomplished by mounting brackets 11 and 11' respectively and by machine screws 11a and 11b. Thus, the clamping jaws cannot journal around the pins as shown in FIGS. 1 and 2. Accordingly, it is possible to apply a testing force that is either a tensile force or a compression force in the apparatus of FIG. 3. The connection of the test sample 1" in FIG. 3 to the holding element 14 may be accomplished either as described above with reference to FIG. 1 or with reference to FIG. 2.

The connection of the clamping jaws 13e and 13f to the machine frame by the machine screws provides a form-locking and force-locking connection so that either tensile or compression forces may be applied to the test sample 1", while still avoiding the application of bending moments to the test sample by maintaining the gap G.

Figure 4:
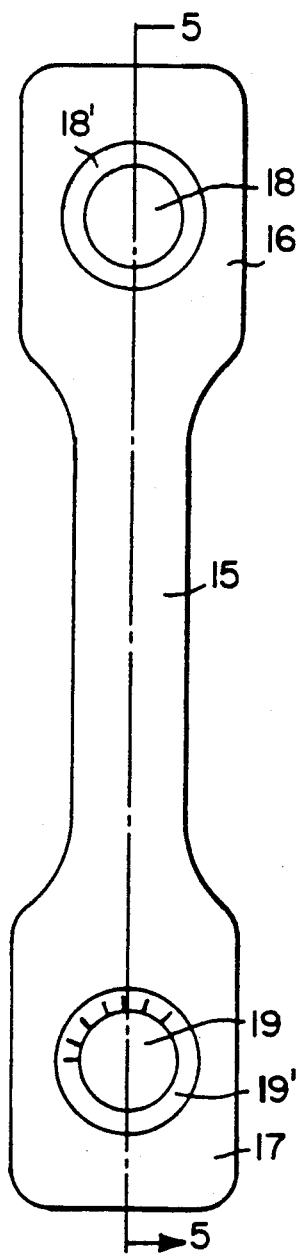
FIG. 4 illustrates a plan view of a flat test sample according to the invention provided with through-bores having conical surfaces in the ends of the test sample.
Figure 5:
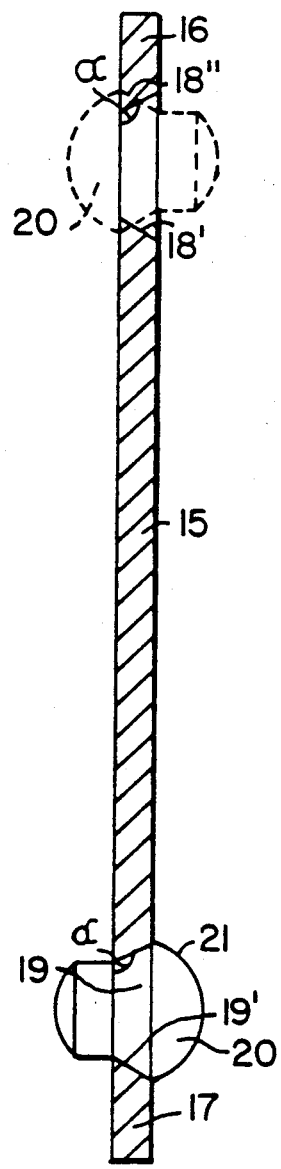
FIG. 5 is a sectional view along section line 5—5 in FIG. 4.

FIGS. 4 and 5 illustrate together a test sample 15 with widened ends 16 and 17. Each end is provided with a respective through-bore 18, 19 having slanted conical walls 18' and 19'. These conical walls 18' and 19' slope in the same direction as shown in full lines in FIG. 5. However, it is also possible that these conical walls slope in opposite directions as shown at 18" and 19' in FIG. 5. The sloping in opposite directions is preferred for a test sample which is to be tested both by tensile forces and compression forces. In that case, the slanting in opposite directions makes sure to hold the sample without play. However, the slanting angle α may be selected small enough to assure a self-locking feature between the sample and the respective holding element 20 shown also in FIG. 6. Preferably, the slanting angle α is within the range 3° to 10°.

Figure 6:
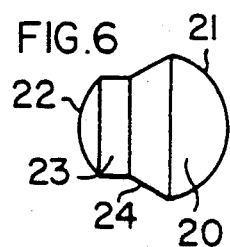
FIG. 6 shows a holding element for cooperation with the test sample of FIGS. 4 and 5.

The holding element 20 of FIG. 6 has two spherical surfaces 21 and 22 interconnected by a cylindrical section 23 having an outer diameter fitting without play into the inner diameter of the through-bores 18, 19. The cylindrical section 23 adjoins a conical or frustum shaped section 24 having a slanting angle corresponding to the slanting angle α. The construction of the holding element 20 is preferably such that the same holding element can be used regardless of the direction of the slant as shown at 18' or 18". FIG. 5 shows the same holding element 20 inserted from one side at the lower end of the sample and the dashed lines at the upper end of FIG. 5 show the insertion from the opposite side. The just described features prevent relative motions between the sample 15 and the holding elements 20 in directions perpendicularly to the load direction. Thus, a connection free of play between the holding and the sample is assured to permit the alternating application of compression and tension loads. Further, the connection between the holding element and the sample may be reinforced by an adhesive bond, either at certain points around the circumference of the holding element, or completely around the holding element.

Although the invention has been described with reference to specific example embodiments, it will be appreciated, that it is intended to cover all modifications and equivalents within the scope of the appended claims.

What I claim is:

1. An apparatus for clamping a test sample having a sample thickness, comprising first and second clamping jaws, spherical segment recesses facing each other in said clamping jaws, a single piece sample holding sphere having spherical surfaces fitting into said spherical segment recesses for clamping said sample holding sphere when said clamping jaws are pressed toward each other, said sample holding sphere having a bore extending in a sample holding direction through said sphere, said test sample having an end for passing through said bore, and means for tightly holding said end of said test sample in said bore to secure said test sample through said sample holding sphere to said clamping jaws, said sample holding sphere having a dimension, relative to said spherical segment recesses, sufficient to form a gap between said clamping jaws, said gap having a gap width larger than said sample thickness for keeping said test sample out of direct contact with said clamping jaws to avoid an application of a bending moment to said test sample while permitting an application of a tension or compression force to said test sample.

2. The apparatus of claim 1, wherein said sample holding sphere having said spherical surfaces and said bore is made of a material selected from the group consisting of steel, ceramics, hard metal, and fiber composite materials.

3. The apparatus of claim 1, further comprising a clamping ring for holding together said first and second clamping jaws, so that said first spherical surfaces of said sample holding sphere are received in said spherical segment recesses of said clamping jaws in a manner free of play.

4. The apparatus of claim 3, wherein said clamping jaws have slanted surfaces, said clamping ring having a correspondingly slanting surface for cooperation with the slanted surfaces of said clamping jaws for pressing said clamping jaws together by a wedging action.

5. The apparatus of claim 1, further comprising mounting means for said clamping jaws, said mounting means comprising a mounting fork and a support pin for securing said clamping jaws in said mounting fork, and means for securing said mounting fork to a machine member.

6. The apparatus of claim 1, wherein at least one of said spherical surfaces of said sample holding sphere and said spherical segment recesses comprise a coating having a low friction coefficient.

7. The apparatus of claim 1, further comprising lubricating means between said spherical segment recesses and said spherical surfaces of said sample holding sphere.

8. An apparatus for clamping a test sample having a sample thickness, comprising first and second clamping jaws, spherical segment recesses facing each other in said clamping jaws, single piece sample holding means each having spherical surfaces fitting into said spherical segment recesses for clamping said single piece sample holding means when said clamping jaws are pressed toward each other, each of said single piece sample holding means further having a ring surface for holding an end of said test sample to secure said test sample through said single piece sample holding means to said clamping jaws, said ring surface extending around said single piece sample holding means between said spherical surfaces, said test sample having an end with a through-bore in which said ring surface of said sample holding means is received, said spherical surfaces having a dimension, relative to said spherical segment recesses, sufficient to form a gap between said clamping jaws, said gap having a gap width larger than said sample thickness for keeping said test sample out of direct contact with said clamping jaws to avoid an application of a bending moment to said test sample while permitting an application of a tension or compression force to said test sample.

9. The apparatus of claim 8, wherein said ring surface is a ground surface having a cylindrical configuration, and wherein said through-bore in said end of said test sample has walls shaped so that said cylindrical ground surface fits into said through-bore without play.

10. The apparatus of claim 8, wherein said ring surface is a conical, ground surface having a slanting angle small enough to assure a self-locking effect in response to a load application between said test sample and said sample holding means, said self-locking effect being effective against relative movements in a direction across the direction of load application.

11. The apparatus of claim 10, wherein said slanting angle at one end of said test sample is directed to slant in a direction opposite to a slant of the respective angle at the opposite end of said test sample.

12. The apparatus of claim 11, wherein said slanting angle is within the range of 3° to 10°.

13. The apparatus of claim 8, wherein said sample holding means comprise holding elements each having two spherical segments, and a cylindrical ring surface between said two spherical segments, said cylindrical ring surface cooperating with a through-bore in an end of said test sample for holding said test sample.

14. The apparatus of claim 13, wherein said two spherical segments form a complete sphere with said cylindrical ring surface formed in an equator of said complete sphere.

15. The apparatus of claim 8, wherein said sample holding means comprise holding elements each having a cylindrical section, a conical section, and two spherical segments, said conical section cooperating with a conical through-bore in an end of said test sample for holding said test sample.

* * * * *